US009693828B2

(12) United States Patent
Aime et al.

(10) Patent No.: US 9,693,828 B2
(45) Date of Patent: Jul. 4, 2017

(54) COMPOSITION COMPRISING ACETIC ANHYDRIDE AND A GADOLINIUM COMPLEX, AND METHOD FOR THE USE IN HYPERPOLARISATION IN MRI ANALYSIS

(71) Applicant: BRACCO IMAGING S.P.A., Milan (IT)

(72) Inventors: Silvio Aime, Carignano (IT); Sonia Colombo Serra, Vigliano Biellese (IT); Pernille Rose Jensen, Copenhagen (DK); Magnus Karlsson, Malmo (SE); Mathilde H. Lerche, Frederiksberg C (DK); Fabio Tedoldi, Marzano (IT); Massimo Visigalli, Settala (IT)

(73) Assignee: BRACCO IMAGING S.P.A., Milan (IT)

( * ) Notice: Subject to any disclaimer, the term of this patent is extended or adjusted under 35 U.S.C. 154(b) by 564 days.

(21) Appl. No.: 14/362,447

(22) PCT Filed: Dec. 3, 2012

(86) PCT No.: PCT/EP2012/074292
§ 371 (c)(1),
(2) Date: Jun. 3, 2014

(87) PCT Pub. No.: WO2013/083535
PCT Pub. Date: Jun. 13, 2013

(65) Prior Publication Data
US 2014/0343402 A1    Nov. 20, 2014

(30) Foreign Application Priority Data
Dec. 5, 2011   (EP) .................................... 11191872

(51) Int. Cl.
| *A61K 49/10* | (2006.01) |
| *A61B 5/05* | (2006.01) |
| *G01R 33/28* | (2006.01) |
| *A61B 19/00* | (2006.01) |
| *A61B 5/055* | (2006.01) |
| *A61B 34/20* | (2016.01) |
| *A61B 90/00* | (2016.01) |

(52) U.S. Cl.
CPC .......... *A61B 19/5244* (2013.01); *A61B 5/055* (2013.01); *A61B 34/20* (2016.02); *A61K 49/106* (2013.01); *A61K 49/108* (2013.01); *G01R 33/286* (2013.01); *A61B 2090/374* (2016.02)

(58) Field of Classification Search
CPC .... A61K 49/10; A61K 49/108; A61K 49/106; G01R 33/5601; G01R 33/286; A61B 19/5244; A61B 5/055; A61B 2019/5236; A61B 34/20; A61B 2090/374
See application file for complete search history.

(56) References Cited

U.S. PATENT DOCUMENTS

| 6,466,814 B1 | 10/2002 | Ardenkjaer-Larsen et al. |
| 2002/0004072 A1 | 1/2002 | Thomas |
| 2008/0095713 A1 | 4/2008 | Thaning |
| 2008/0287774 A1 | 11/2008 | Katz-Brull |
| 2008/0292551 A1 | 11/2008 | Thaning et al. |
| 2009/0148432 A1 | 6/2009 | Higuchi |
| 2010/0158810 A1* | 6/2010 | Lisitza .................. A61K 49/10 424/9.3 |
| 2010/0190967 A1 | 7/2010 | Gloegaard et al. |
| 2013/0096420 A1 | 4/2013 | Aime et al. |
| 2014/0257085 A1 | 9/2014 | Aime et al. |

FOREIGN PATENT DOCUMENTS

| EP | 1544634 A1 | 6/2005 |
| JP | 2009527768 | 7/2009 |
| WO | 88-10419 A1 | 12/1988 |
| WO | 90-00904 A1 | 2/1990 |
| WO | 91-12024 A1 | 8/1991 |
| WO | 93-02711 A1 | 2/1993 |
| WO | 96-39367 A1 | 12/1996 |
| WO | 98-58272 A1 | 12/1998 |
| WO | 9924080 A1 | 5/1999 |
| WO | 99-35508 A1 | 7/1999 |
| WO | 01-96895 A1 | 12/2001 |
| WO | 0237132 | 5/2002 |
| WO | 2007044867 A2 | 4/2007 |
| WO | 2007-064226 A2 | 6/2007 |
| WO | 2007136439 A2 | 11/2007 |
| WO | 2010037771 A1 | 4/2010 |
| WO | 2011-124672 A1 | 10/2011 |

OTHER PUBLICATIONS

European Search Report for European application No. EP11184825.5, mail date Feb. 10, 2012.
PCT International Preliminary Report on Patentability for PCT/EP2012/074292, mail date Jun. 19, 2014.
PCT international Search Report for PCT/EP2012/070187, mail date Dec. 4, 2012.
PCT Written Opinion for PCT/EP2012/070187, mail date Dec. 4, 2012.
PCT International Preliminary Report on Patentability for PCT/EP2012/070187, mail date Apr. 15, 2014.
PCT International Search Report for PCT/EP2012/074292, mail date Jan. 30, 2013.
PCT Written Opinion for PCT/EP2012/074292, mail date Jan. 30, 2013.
Aime, Silvio et al., "Synthesis and NMRD Studies of Gd3+ Complexes of Macrocyclic Polyamino Polycarboxylic Ligands Bearing beta-Benzyloxy-alpha-propionic Residues", Inorganic Chemistry, American Chemical Society, Easton, US, vol. 31, No. 6, Mar. 18, 1992, pp. 1100-1103, XP002120082, ISSN: 0020-1669, DOI: 10.1021/IC00032A035.

(Continued)

Primary Examiner — Michael G Hartley
Assistant Examiner — Leah Schlientz
(74) Attorney, Agent, or Firm — Vivicar Law, PLLC

(57) ABSTRACT

The present invention generally relates to a composition comprising acetic anhydride, a DNP agent and a gadolinium complex and its use for the preparation of hyperpolarised imaging agent for MR diagnostic analysis.

18 Claims, 4 Drawing Sheets

(56) References Cited

OTHER PUBLICATIONS

Gallagher, Ferdia A. et al., "Production of hyperpolarized [1,4-13C2]malate from [1,4-13C2]furmarate is a marker of cell necrosis and treatment response in tumors", Proceedings of the National Academy of Sciences, Jan. 1, 2009, XP055045201, ISSN: 0027-8424, DOI: 10.1073/pnas.0911447106, pp. 19801-19806.

Gallagher, Ferdia A. et al., "Detection of tumor glutamate metabolism in vivo using 13C magnetic resonance spectroscopy and hypepolarized [1-13C]glutamate", Magnetic Resonance in Medicine, vol. 66, No. 1, Feb. 17, 2011, pp. 18-23, XP055045198, ISSN: 0740-3194, DOI: 10.1002/mrm.22851.

Hovland, Ragnar et al., "Preparation and In Vitro Evaluation of Godota-(BOM)4; A Novel Angiographic MRI Contrast Agent", Org. Biomol Chem., vol. 1, Apr. 10, 2003, pp. 1707-1710, XP002672385.

Viale, Alessandra et al., "Current concepts on hyperpolarized molecules in MRI", Current Opinion in Chemical Biology, Current Biology Ltd., London, GB, vol. 14, No. 1, Feb. 1, 2010, pp. 90-96, XP026895607, ISSN: 1367-5931, DOI: 10.1016/J.CBPA.2009.10.021.

Wilson, David M. et al., "Generation of hyperpolarized sustrates by secondary labeling with [1,1-C-13] acetic anhydride", Proceedings of the National Academy of Sciencies of USA, National Academy of Science, Washington, DC; US, vol. 106, No. 14, Apr. 7, 2009, pp. 5503-5507, XP002641409, ISSN: 0027-8424, DOI: 10.1073/PNAS.08109106.

European Search Report for application No. EP11191872.8, mail date Apr. 12, 2012.

Goldman, Maurice et. al., Design and implementation of 13C hyper polarization from ara-hydrogen, for new MRI contrast agents, Comptes Rendus-Chimie, Elsevier, Paria, FR, vol. 9, No. 3-4, Mar. 1, 2006, pp. 357-363, XP024979705.

Goldman, Maurice et. al., Hyperpolarization of 13C through order transfer from parahydrogen: A new contrast agent for MRI, Magnetic Resonance Imaging, Elsevier Science, Tarrytown, NY, US, vol. 23, No. 2, Feb. 1, 2005, pp. 153-157, XP004843472.

Golman, K. et. al., Molecular imaging using hyperpolarized 13C, The British Journal of Radiology 2003, vol. 76, Spec No. 2, 2003, pp. S118-S127, XP002538147.

"Hydrolysis" http://chem.libretexts.org/Core/Physical_and_Theoretical_Chemistry/Equilibria/Solubilty/Hydrolysis, Oct. 2015.

Jamin et al., Magnetic Resonance in Medicine, 2009, 62, pp. 1300-1304.

Joo, Ferenc, Aqueous biphasic hydrogenations, Accounts of Chemical Research Sep. 2002, vol. 35, No. 9, Sep. 2002, pp. 738-745, XP002538144.

Office Action for Japanese App. No. 2013-503125, mail date Oct. 7, 2014 (with English language Office Action Summary) [B0651].

PCT international Search Report and Written Opinion for PCT/EP2011/055485, mail date Jun. 30, 2011.

Reineri, Francesca et. al., New Hyperpolarized contrast agents for 13C MRI from para-hydrogenation of pligooxyethylenic alkynes, Journal of the American Chemical Society 20081112 American Chemical Society US, vol. 130, No. 45, Nov. 12, 2008, pp. 15047-15053, XP002538148.

Wang, Chao et. al., Broader, greener, and more efficient: recent advances in asymmetric transfer hydrogenation, chemistry, An Asian Journal Oct. 6, 2008, vol. 3, No. 10, Aug. 27, 2008, pp. 1750-1770, XP002538145.

\* cited by examiner

Complex (I)

Complex (II)

Complex (III)

COMPOSITION COMPRISING ACETIC ANHYDRIDE AND A GADOLINIUM COMPLEX, AND METHOD FOR THE USE IN HYPERPOLARISATION IN MRI ANALYSIS

CROSS-REFERENCE TO RELATED APPLICATIONS

This application is the national stage application of corresponding international application number PCT/EP2012/074292, filed Dec. 3, 2012, which claims priority to and the benefit of European application no. 11191872.8, filed Dec. 5, 2011, all of which are hereby incorporated by reference in their entirety.

The present invention generally relates to a composition comprising acetic anhydride, a DNP agent and a gadolinium complex and its use for the preparation of a hyperpolarised imaging agent for MR diagnostic analysis.

BACKGROUND OF THE INVENTION

MRI is a non invasive technique with broad diagnostic value. The technique has gained wide clinical acceptance and is of great importance in diagnostic medicine. However, despite significant technological advancements (increasing field strength and improvement in technology), applications of MRI are limited by an intrinsically low sensitivity.

Some alternatives to enhance its sensitivity have been developed which involve ex-vivo nuclear spin polarisation of agents, prior to administration and consequent in-vivo MR signal measurement.

EP1544634 discloses some of said alternative techniques, comprising among others, Dynamic Nuclear Polarisation (DNP), Para Hydrogen Induced (PHI) polarisation and Polarisation Transfer (PT) from a hyperpolarised noble gas.

WO9935508 describes a method for obtaining hyperpolarised high T1 agents by dynamic nuclear polarisation (DNP) whereby polarisation of a sample is carried out by a polarising agent or so-called DNP agent, which is a compound comprising unpaired electron.

WO2007064226 generally describes the use of paramagnetic metal ions, optionally added in chelated form, to enhance the hyperpolarisation level of a substrate, when subjected to hyperpolarisation MRI experiments.

We have now found that when a composition comprising acetic anhydride, a DNP agent and a suitable gadolinium complex of formula (A), is used in DNP experiments, an unexpectedly high degree of polarisation of the acetic anhydride system can be achieved. Even further, when the hyperpolarised acetic anhydride thus obtained is contacted with an aqueous carrier, the anhydride is converted to acetic acid, maintaining the high degree of polarisation and thus employable e.g. as MRI contrast agent.

Hence, according to the invention, the gadolinium complex of formula (A) is particularly advantageous when used as DNP hyperpolarisation enhancer for acetic anhydride based systems. For these and other advantages, which may be better appreciated by the skilled person upon reading the detailed description of the invention, the present invention provides a substantial innovative contribution over the state of the art.

SUMMARY OF THE INVENTION

A first aspect of the invention refers to a composition comprising:
acetic anhydride,
a DNP agent, and
a gadolinium complex of formula (A):

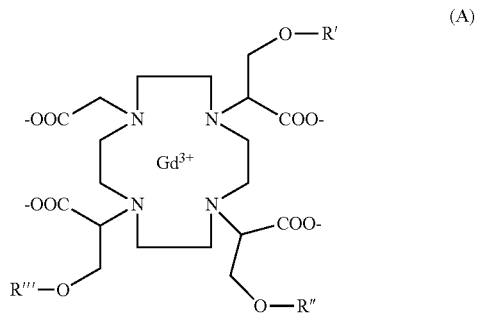

wherein:
R', R" and R'" are independently selected from: optionally substituted phenyl, $(C_1-C_6)$alkylene-phenyl and $C_6-C_{10}$ heterocyclic ring.

It is a further aspect of the invention the use of said composition for the preparation of hyperpolarised acetic anhydride in DNP experiment. In another aspect, the invention refers to the use of the gadolinium complex of general formula (A) as hyperpolarisation enhancer in dynamic nuclear polarisation (DNP) experiments.

The invention also relates to a process for preparing hyperpolarised acetic acid for the use in a method of magnetic resonance investigation, comprising:

a) subjecting the composition of the present invention as previously defined to dynamic nuclear polarisation (DNP) methods to obtain hyperpolarised acetic anhydride; and b) contacting the hyperpolarised acetic anhydride of step a) with an aqueous carrier to convert said hyperpolarised acetic anhydride to hyperpolarised acetic acid; and optionally c) removing the gadolinium complex of formula (A) and the DNP agent.

It is herein also provided a method for operating an MRI system comprising the steps of:

a) submitting a subject, which has been positioned in said MRI system and treated with hyperpolarised acetic acid obtained according to the above process, to a radiation frequency selected to excite nuclear spin transitions in a non-zero nuclear spin nuclei of said active substrate; and b) recording a MR signal from said excited nuclei.

In a further aspect, the present invention relates to a method for operating a MRI system comprising the steps of:

a) submitting a subject pre-treated with hyperpolarised acetic acid obtained according to the above process, which has been positioned in said MRI system, to a radiation frequency selected to excite nuclear spin transitions in a non-zero nuclear spin nuclei of said active substrate; and b) recording a MR signal from said excited nuclei.

DETAILED DESCRIPTION OF THE INVENTION

Figure 1:
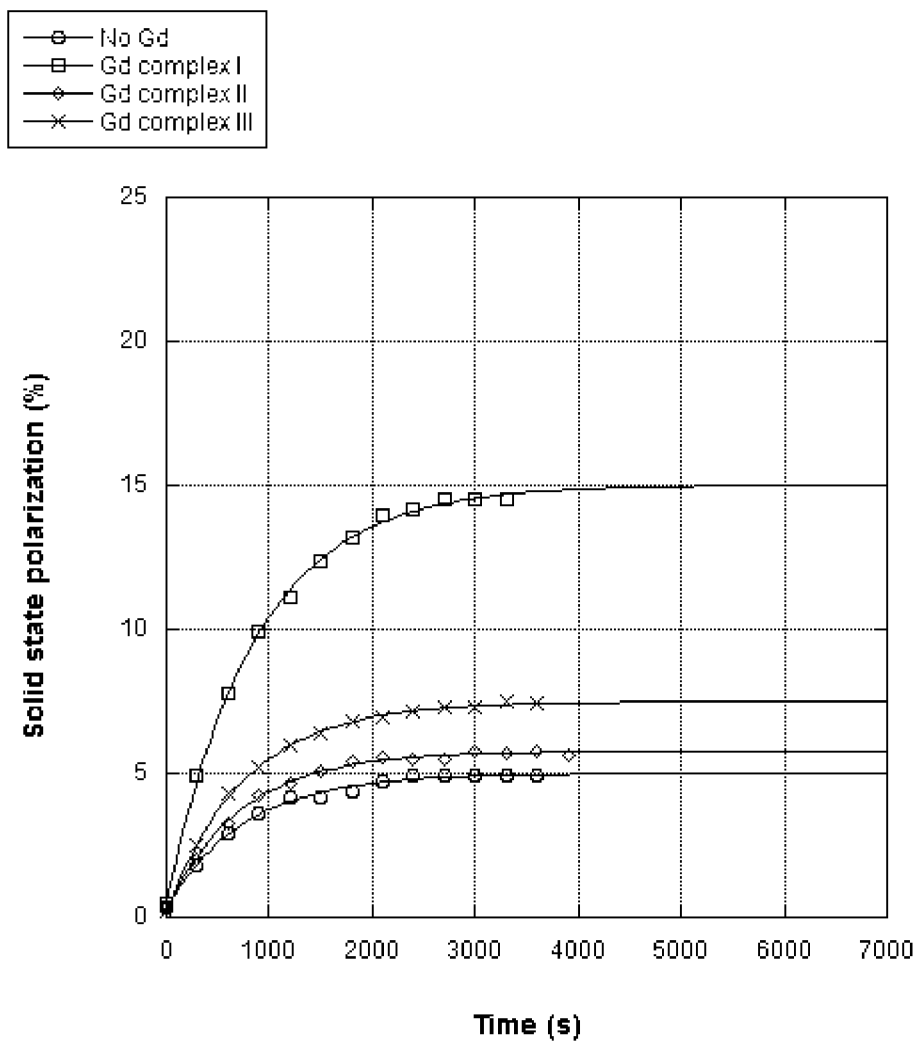
FIG. 1: Acetic anhydride solid state polarisation build up curves. The figure shows the degree of hyperpolarisation obtainable by adding three different gadolinium complexes to a mixture of acetic anhydride and Finlandic radical, in DNP experiments.

The term (C1-C6)alkylene-phenyl comprises within its meaning a bivalent linear or branched alkenyl group having from 1 to 6 atom carbons, such as: methylene, ethylene, propylene and the like, linked to an optionally substituted phenyl group.

The term optionally substituted phenyl group comprises within its meaning a phenyl ring optionally substituted with e.g. one or more substituents such as C1-C6 linear or branched alkyl groups like, for instance, methyl, ethyl, propyl and the like.

The term C6-C10 heterocyclic ring comprises within its meaning an aromatic or aliphatic carbon ring having from 6 to 10 atoms, interrupted by one or more heteroatoms selected from: N, O, P and S.

The term "polarising agent" or "DNP agent" or "radical" comprises within its meaning a compound comprising unpaired electron. During the DNP process, energy, generally provided in the form of microwave irradiation, initially excites the DNP agent. Upon decay to the ground state, a transfer of polarisation occurs from the unpaired electron off the DNP agent to the NMR active nuclei of the sample, i.e. the acetic anhydride.

The term "glass form" comprises within its meaning a solid solution or an amorphous (non-crystalline) solid form.

The term "glass-forming agent" or "glassing agent" comprises within its meaning a compound which prevents crystallization and promotes the formation of a glass form.

The expression "aqueous carrier" comprises within its meaning any aqueous solvent, solvent mixtures or solutions that are tolerated by the human or non-human animal body, for use in in-vivo diagnostic applications.

Generally, the carrier is sterile and physiologically tolerable, such as sterile water, purified water such as water for injection (WFI), physiological saline solution, optionally properly buffered.

In this respect, in some cases, the obtained aqueous solution (comprising the hyperpolarised acetic anhydride) may subsequently be admixed with further additives in order to render it physiologically acceptable for in-vivo diagnostic applications. Examples of suitable additives are pH regulating agents such as organic or inorganic bases (e.g. alkaline metal bases) or organic or inorganic acids or buffers.

In a first aspect, the invention relates to a composition for the use in DNP experiments for the preparation of hyperpolarised acetic anhydride, comprising:

acetic anhydride, a
DNP agent, and
a gadolinium complex of formula (A):

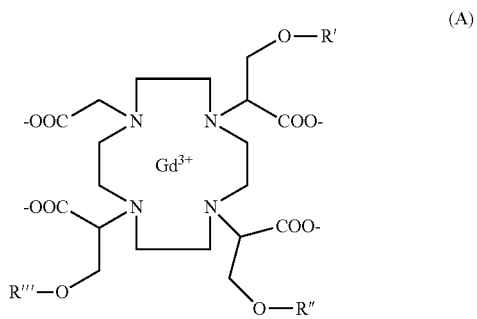

wherein:
R', R" and R'" are independently selected from: optionally substituted phenyl, $(C_1-C_6)$alkylene-phenyl and $C_6-C_{10}$ heterocyclic ring.

Preferably R', R" and R'" are the same.

In a preferred embodiment, the composition is a liquid solution having a concentration of from about 2M to about 12 M with respect to the acetic anhydride, preferably from 5 to 10 M, even more preferably from 8 to 10M.

In a further embodiment, the present composition comprises: acetic anhydride, a DNP agent as herewith set forth and a gadolinium complex of the above formula (A), wherein R is the same a (C1-C6)alkenyl-phenyl, more preferably, the gadolinium complex of formula (A) is [[α1,α4,α7-tris[(phenylmethoxy)methyl]-1,4,7,10-tetraazacyclododecane-1,4,7,10-tetraacetato(4-)]gadolinate(1-)]hydrogen, of formula:

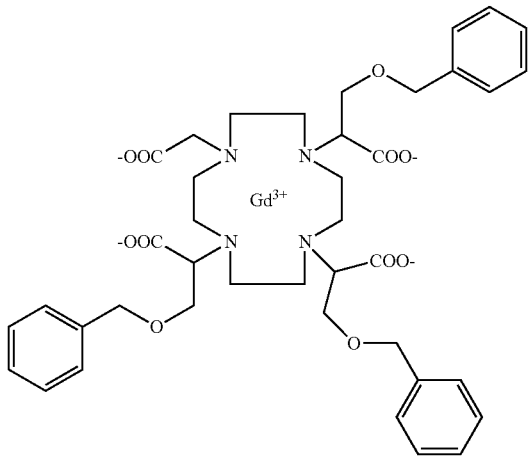

Formula I

In this respect, the gadolinium complex of formula (I) can be prepared e.g. according to Aime S. et al. Inorg. Chem. 1992, 31, 1100-1103.

Preferred concentrations of the gadolinium complex are from 0.5 mM to 4 mM, more preferably from 1 mM to 2.5 mM.

As regards the DNP agent, commonly known as "radical", it should be stable in the reaction media of choice, and at least partially soluble in the system in order to obtain a homogenous distribution and an optimal concentration of the electron spin relative to the nuclear spin. Typically, the polarising agent is added in an amount of from 5 mM to 50 mM to the mixture undergoing DNP, more preferably from 8 to 18 mM. Due in particular to their efficient polarisation properties, the use of trityl radicals as polarising agents is preferred, such as, for instance those described in WO-A-99/35508, WO-A-88/10419, WO-A-90/00904, WO-A-91/12024, WO-A-93/02711 or WO-A-96/39367 and herein included by reference.

According to a still preferred embodiment, a radical of the following general formula (B) can advantageously be employed as polarising agent:

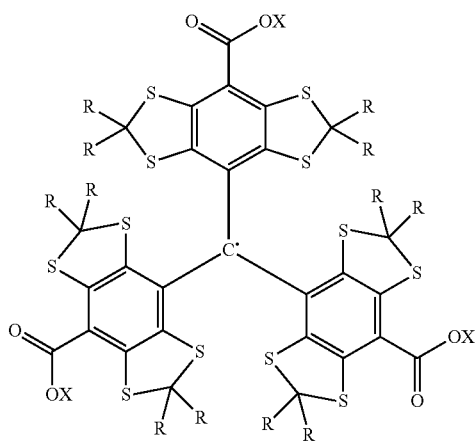

Formula (B)

wherein:

R the same or different, represents a straight chain or branched C1-C6-alkyl group optionally substituted by one or more hydroxyl group, methoxy group, or a group of formula —$(CH_2)_n$—O—R2, wherein n is 1, 2 or 3;

R2 is a straight chain or branched C1-C6-alkyl group, optionally substituted by one or more hydroxyl groups or methoxy groups; and X is independently selected from: hydrogen H, an alkaline metal, e.g. Na, K, Cs, an optionally substituted straight or branched C1-C6 alkyl group, optionally interrupted by Sulphur or Oxygen atoms, and an optionally substituted aliphatic or aromatic C3-C8 cyclic group or hetero group.

Preferably, said radical is a compound of the above formula (B) which is soluble in acetic anhydride e.g. a compound of formula (B), wherein X is hydrogen, or wherein X is selected from hydrophobic moieties such as methyl, —CD3, ethyl, tert-butyl or phenyl.

The selected DNP agent or radical is preferably the trityl radical, e.g. the compound of the above formula (B) wherein R is CH3 or CD3, generally present in the composition at a concentration from 5 mM to 25 mM, whereas, preferred concentrations are from 10 mM to 15 mM.

The above mentioned radicals of general formula (B) are known and commercially available (e.g. from Sigma-Aldrich).

The present composition comprising the acetic anhydride, a DNP agent, e.g. of formula (B), and a paramagnetic complex of formula (A) can be prepared by mixing together the three components, e.g. by means of methods known in the art, such as stirring, vortexing and/or sonication.

Advantageously, the present composition does not require the presence of any additional glassing agent (such as glycerol or DMSO) since upon freezing the present composition spontaneously forms a glass, suitable for the DNP experiment.

Figure 4:
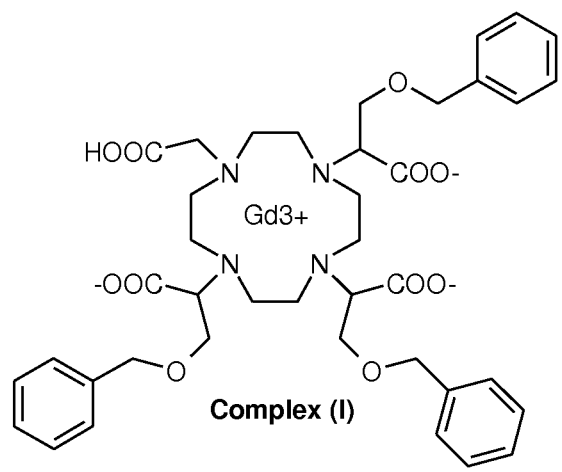
FIG. 4: Gadolinium complexes I, II, III formulae.
Figure 4:
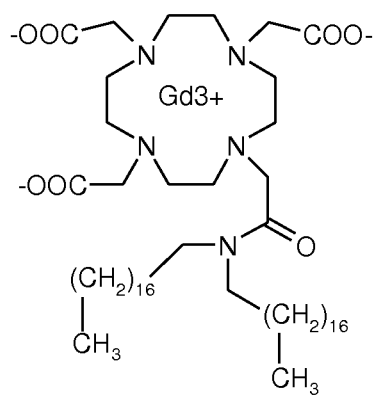
Figure 4:
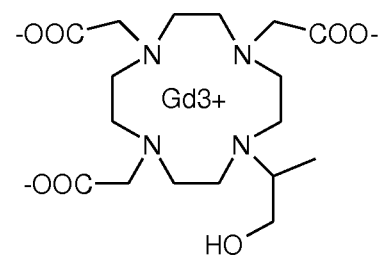

Even further, as supported in the herein below experimental part, the composition of the invention when subjected to DNP experiments, allows the preparation of hyperpolarised acetic anhydride with an unexpectedly high degree of polarisation, with respect to similar mixtures comprising different gadolinium complexes, such as e.g. Gd-DOTAM of formula (II) or a gadolinium complex of formula (III) as indicated in FIG. 4. In fact, the use of the complex of formula (I) ([[α1,α4,α7-tris[(phenylmethoxy)methyl]-1,4,7,10-tetraazacyclododecane-1,4,7,10-tetraacetato(4-)]gadolinate(1-)]hydrogen) in the presence of a DNP agent as formerly described, allows the preparation of acetic anhydride with a degree of polarisation 2 times higher than the degree otherwise obtainable by using Gd-DOTAM (II) or the complex of formula (III), without impairing the polarisation time, as shown in Figure I. The result is even more surprising when considering a similar system wherein the acetic anhydride is replaced by butyric anhydride. The anhydrides are polar aprotic liquids which are in fact able to form a glass form by themselves (e.g. without the addition of any glassing agent) upon freezing.

Figure 2:
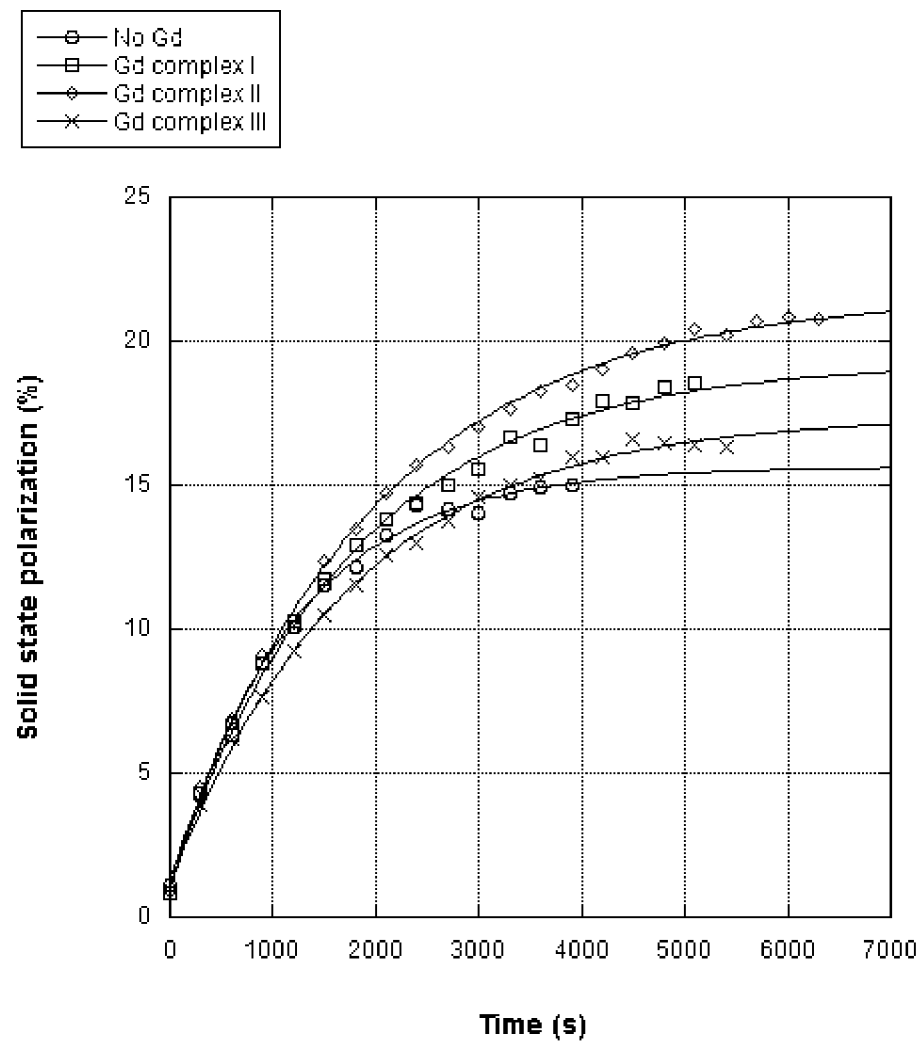
FIG. 2: Butyric anhydride solid state polarisation build up curves. The figure shows the degree of hyperpolarisation obtainable by adding three different gadolinium complexes to a mixture of butyric anhydride and Finlandic radical, in DNP experiments.

However, in the case of butyric anhydride, and contrary to what happen for the similar acetic anhydride system, the degree of polarisation obtained using the complex of formula (I) is basically the same obtainable by using the other gadolinium complexes of formula (II) and (III) (i.e. 1,5-1.7 time higher) as clearly indicated in the FIG. 2 herein below. This means that the present composition comprising the complex of general formula (A), as above defined, as DNP hyperpolarisation enhancer can be advantageously used in a process for the preparation of hyperpolarised acetic anhydride to be further used as precursor for the preparation of hyperpolarised acetic acid as herein below described. Conveniently in fact, because of the high degree of polarisation achievable, the hyperpolarised acetic anhydride obtained when the present composition is used in DNP experiments, can be contacted with an aqueous carrier to be hydrolyzed to acetic acid, substantially maintaining the high degree of polarisation Therefore, in a further aspect, the invention refers to a process for the preparation of hyperpolarised acetic acid, said process comprising the steps of:

a) subjecting the composition of the present invention as previously defined to dynamic nuclear polarisation (DNP) methods to obtain hyperpolarised acetic anhydride; and b) contacting the hyperpolarised acetic anhydride of step a) with an aqueous carrier to convert said hyperpolarised acetic anhydride to hyperpolarised acetic acid; and optionally c) removing the gadolinium complex of formula (A) and the DNP agent.

In step a), the composition of the present invention, comprising acetic anhydride, a DNP agent and a gadolinium complex of formula (A), preferably of formula (I), is hyperpolarised by Dynamic Nuclear Polarisation (DNP), as described, for instance, in WO 98/58272 and WO0196895. Practically, the composition is cooled and/or frozen, in such a way that a glass form is formed. As afore mentioned, advantageously, and differently from other similar organic substrates, the present composition does not require the addition of any glass forming agent since the acetic anhydride system spontaneously forms a glass upon freezing. Preferably, the frozen composition is irradiated at a frequency comprised from about 94 GHz to about 200 mW. The thus hyperpolarised acetic anhydride composition may be monitored using e.g. MR spectroscopy or MRI techniques, as commonly used in the art.

The solid polarised acetic anhydride, is then converted into liquid hyperpolarised acetic acid, according to step b) of the present process. Typically, the solid hyperpolarised composition obtained after step a) is dissolved in an appropriate aqueous carrier, optionally containing additives such as buffers, pH regulating agents, and the like. Preferably, the hyperpolarised acetic anhydride system is dissolved in an aqueous carrier, to result in a physiologically tolerable solution comprising hyperpolarised acetic acid. In this respect, preferred aqueous carriers are selected from: saline, water, aqueous solutions containing a suitable amount of a base, such as NaOH or other organic or inorganic compounds with basic aqueous reaction (e.g. tromethamine or trisodium phosphate), or of an inorganic or organic acid such as phosphoric acid, hydrochloric acid, citric acid or acetic acid, capable of promoting the hydrolysis. Typically, the base is present in an amount of about 1 to 5 mole equivalents to the anhydride, preferably about 2 to 4 mole.

The aqueous carrier is added to the anhydride mixture in order to have a quantitative transformation of the anhydride into the acid, wherein "quantitative transformation" means that the conversion is of at least 20%, preferably 50% or more, even more preferably 75%, 90% or more. After the dissolution step, the active acetic acid is present in the aqueous solution and the resulting pH may be adjusted at physiologically acceptable values generally by adding suitable acid or basic buffers thereto. The precise concentration will of course depend upon a range of factors such as, inter alia, toxicity and administration route. In general, optimal concentrations will in most cases lie in the range from 10 mM to 150 mM, particularly from 40 to 80 mM.

According to the last step of the present process, the gadolinium complex of formula (A) and/or the DNP agent, along with any reaction products thereof, are optionally removed from the final composition. If the hyperpolarised acetic acid thus obtained is intended to be used as a MR imaging agent in living human or animal being, both the trityl radical and the paramagnetic metal complex are preferably removed from the liquid composition. In this respect, upon dissolution of the solid hyperpolarised acetic anhydride composition the DNP agent and/or the paramagnetic metal ion might precipitate and thus may be easily separated from the liquid by filtration. If no precipitation occurs or if such precipitation partially occurs, the DNP agent and the chosen paramagnetic complex may be removed by chromatographic separation techniques according to methods known in the art, such as reversed phase liquid chromatography and the like.

After removal of the paramagnetic complex of formula (A) and/or the DNP agent, or reaction derivatives thereof, the liquid sample may be checked for residual paramagnetic metal ion and/or DNP agent traces, by e.g. UV/visible absorption measurements or electrochemical detection, fluorescent measurements and the like.

In a preferred embodiment, the acetic anhydride is enriched with non-zero nuclear spin nuclei, such as 13C. The term "enriched" means that the concentration of the non-zero spin nuclei in the compound is above the typical value of natural abundance of said nuclei, preferably above at least 10% of natural abundance, more preferably above at least 25%, and even more preferably above at least 75% of its natural abundance and most preferably above at least 90% of its natural abundance. The enrichment will in particular be concentrated on an atom position, for which a chemical transformation of the molecule, or a chemical or magnetic changes of the environment of the molecule, will be measurable as a change of its chemical shift. Said non-zero nuclei confer to the substrate a T1 relaxation time of at least 5 seconds (indicated with s), preferably of at least 10 s, preferably of at least 20 s, preferably of at least 30 s, and even more preferably of at least 40 s, measured in a solution subjected to a magnetic fields of from about 0.5 mT to about 20 T (Tesla). The enrichment may include either selective enrichments of one or more sites within the molecule or uniform enrichment of all sites. To this extent, commercially available enriched acetic anhydride can be suitably employed or, in case, the enrichment can be achieved by chemical synthesis, or biological labeling, according to well known prior art teachings.

As extensively reported, the present invention provides a composition comprising acetic anhydride, a DNP agent and a gadolinium complex of general formula (A), preferably the complex of formula (I), for the preparation of hyperpolarised acetic anhydride with a remarkably high degree of polarisation, and suitable for the use in the preparation of a MRI contrast agent, when converted into the active acetic acid as above explained. In this respect, the dosage of the solution should be kept as low as possible whilst still providing a detectable contrast response. The dosage of the MR imaging substrate obtained according to the present method will vary depending on, for instance, the nature of the tissue or organ of interest and the measuring apparatus.

In particular, the hyperpolarised hydrolysed substrate (i.e. the active acetic acid) can be administered into the vascular system or directly into an organ or muscle tissue, or by subdermal or subcutaneous route, as the case may be. It has to be noted in this respect that the physical features of the solution to be administered (such as the temperature, density and the like) have to be physiologically tolerable in order to reduce the risks associated with the selected route of administration.

It will be clear that the present method should be carried out within the frame of time in which the hyperpolarised acetic acid remains significantly polarised, shortly after being subjected to the chemical conversion of the solid acetic anhydride mixture thereof. This means that the sample, either human or non-human animal body, should be available close to the area in which the polarisation takes place.

Due to the high polarisation level achievable, the present process and the method of the present invention may find clinical application in a variety of imaging investigations such as, but not limited to, the vascular/angiographic imaging, interventional applications, perfusion mapping or metabolic/molecular imaging In particular, in another aspect, the present invention relates to a method for operating an MRI system comprising the steps of:

a) submitting a subject, which has been positioned in said MRI system and treated with a hyperpolarised active acetic acid obtained according to the above process, to a radiation frequency selected to excite nuclear spin transitions in a non-zero nuclear spin nuclei of said active substrate; and b) recording a MR signal from said excited nuclei.

In a further aspect, the present invention relates to a method for operating a MRI system comprising the steps of:

a) submitting a subject pre-treated with a hyperpolarised active acetic acid obtained according to the above process, which has been positioned in said MRI system, to a radiation frequency selected to excite nuclear spin transitions in a non-zero nuclear spin nuclei of said active substrate; and b) recording a MR signal from said excited nuclei.

According to a further aspect, the present invention relates to the use of a gadolinium complex of formula (A) as above defined, for the preparation of hyperpolarised acetic anhydride in dynamic nuclear polarisation (DNP) experiments. As clearly evident from the experimental part herein below, in fact, the use of a complex of formula (A), e.g. wherein R is a benzyl group, (i.e. the compound of formula (I)) results in an unexpected enhancement in the polarisation level when acetic anhydride is subjected to DNP experiment. Contrary to the similar butyric anhydride system, in fact, the gadolinium complex of formula (I) leads to an enhancement of about 2 times in the case of acetic anhydride vs an enhancement of about 1.5 in the case of butyric anhydride.

The following examples are intended to better define the invention, without posing any limitation thereof.

EXPERIMENTAL PART

Materials

Figure 3:
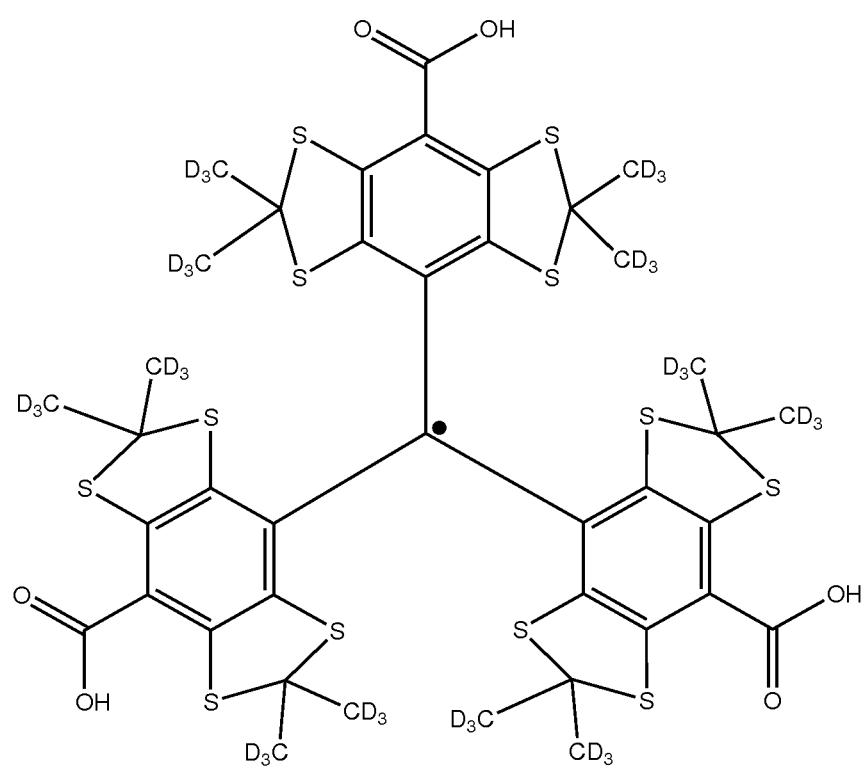
FIG. 3: Finlandic acid radical formula.

The following materials are employed in the subsequent examples:

Finlandic acidTris(8-carboxy-2,2,6,6-tetramethylbenzo[1,2-d:4,5-d']-bis(1,3)dithiol-4-yl), carboxylic acid form, FIG. 3

Gadolinium complex I, [[α1,α4,α7-tris[(phenylmethoxy)methyl]-1,4,7,10-tetraazacyclododecane-1,4,7,10-tetraacetato(4-)]gadolinate(1-)]hydrogen, FIG. 4

Gadolinium complex II [10-[2-(dioctadecylamino)-2-oxoethyl]-1,4,7,10-tetraazacyclododecane-1,4,7-triacetato(3-)]gadolinium, FIG. 4

Gadolinium complex III, [10-(2-hydroxypropyl)-1,4,7,10-tetraazacyclododecane-1,4,7-triacetato(3-)]gadolinium, FIG. 4

Example 1

DNP Preparation of Acetic Anhydride in the Presence of a Trityl Radical as DNP Agent Finlandic acid (1.90 mg, 1.83 μmol) was dissolved in unlabeled acetic anhydride (110 μl, 119.7 mg). Several rounds of sonication and whirling were performed to fully dissolve the radical. The concentration of the radical in this solution was 16.7 mM. A fraction of this solution (30 μl, 32.3 mg) was mixed with 1,1'-13C2 acetic anhydride (10 μl, 11.0 mg, 0.10 μmol) yielding a solution with a radical concentration of 12.5 mM. A sample of this solution (43 mg containing 0.2 mmol 13C) was hyperpolarised with an exponential time constant of 670 s and an end polarisation value of 5%, FIG. 1.

Example 2

DNP Preparation of Acetic Anhydride in the Presence of Gd-Chelate I as Paramagnetic Metal Ion a Trityl Radical as DNP Agent Finlandic acid (6.80 mg, 6.56 μmol) was dissolved in unlabeled acetic anhydride (393 μl, 427 mg). Several rounds of sonication and whirling were performed to fully dissolve the radical. The concentration of the radical in this solution was 16.7 mM. Mortared gadolinium complex II (0.84 mg, 0.79 μmol) was added to the solution. The mixture was ultra-sonicated for 1 minute and then whirl-mixed. This sonication/whirl-mixing procedure was repeated two times after which the solution was centrifuged at 10000 RPM for 3 minutes. A fraction of this solution (30 μl, 32.5 mg) was mixed with 1,1'-13C2 acetic anhydride (10 μl, 11.0 mg, 0.10 μmol) yielding a solution with a radical concentration of 12.5 mM. A sample of this solution (43.3 mg containing 0.2 mmol 13C) was hyperpolarised with an exponential time constant of 690 s and an end polarisation value of 6%, FIG. 1. In comparison to ex. 1 the addition of gadolinium complex II does not change the polarisation properties of the sample significantly.

Example 3

DNP Preparation of Acetic Anhydride in the Presence of Complex (I) as Paramagnetic Metal Ion a Trityl Radical as DNP Agent Finlandic acid (8.94 mg, 8.62 μmol) was dissolved in unlabeled acetic anhydride (516 μl, 566 mg). Several rounds of sonication and whirling were performed to fully dissolve the radical. The concentration of the radical in this solution was 16.7 mM. Mortared gadolinium complex I (0.76 mg, 0.82 μmol) was added to 413 μl of the solution. The mixture was ultra-sonicated for 1 minute and then whirl-mixed. This sonication/whirl-mixing procedure was repeated two times after which the solution was centrifuged at 10000 RPM for 3 minutes. A fraction of this solution (30 μl, 33 mg) was mixed with 1,1'-13C2 acetic anhydride (10 μl, 11.0 mg, 0.10 μmol) yielding a solution with a radical concentration of 12.5 mM. A sample of this solution (43.7 mg containing 0.2 mmol 13C) was hyperpolarised with an exponential time constant of 690 s and an end polarisation value of 15%, FIG. 1. In comparison to ex. 1 the addition of gadolinium complex I increase the end polarisation of the sample by a factor of 2 without increasing the polarisation build-up time.

Example 4

DNP Preparation of Acetic Anhydride in the Presence of Complex III as Paramagnetic Metal Ion a Trityl Radical as DNP Agent Finlandic acid (9.62 mg, 9.28 μmol) was dissolved in unlabeled acetic anhydride (556 μl, 608 mg). Several rounds of sonication and whirling were performed to fully dissolve the radical. The concentration of the radical in this solution was 16.7 mM. Mortared gadolinium complex III (0.35 mg, 0.62 μmol) was added to 313 μl of the solution. The mixture was ultra-sonicated for 1 minute and then whirl-mixed. This sonication/whirl-mixing procedure was repeated two times after which the solution was centrifuged at 10000 RPM for 3 minutes. A fraction of this solution (30 μl, 33 mg) was mixed with 1,1'-13C2 acetic anhydride (10 μl, 11.0 mg, 0.10 μmol) yielding a solution with a radical concentration of 12.5 mM. A sample of this solution (43.5 mg containing 0.2 mmol 13C) was hyperpolarised with an exponential time constant of 750 s and an end polarisation value of 7.5%, FIG. 1. In comparison to ex. 1 the addition of gadolinium complex III results in a small increase of the end polarisation of the sample.

Example 5

DNP Preparation, Dissolution and Hydrolysis of Acetic Anhydride in the Presence of a Trityl Radical as DNP Agent A stock solution of radical was prepared by dissolving Finlandic acid (2.7 mg, 2.6 μmol) in unlabeled acetic anhydride (22.2 mg) yielding a solution with a concentration of 105 µmol/g. A part (2.1 mg) of this stock solution was mixed with 1,1'-$^{13}C_2$ acetic anhydride (15 µl, 17.2 mg, 0.165 mmol) to make a 12.8 mM solution. From this solution a sample (17.1 mg, 0.15 mmol) was hyperpolarised with an exponential time constant of 525 s and an end polarisation value of 5%. The sample was dissolved in 5 ml water with added NaOH (12 M, 39 µl) and allowed to hydrolyze for 15 s and then neutralized by mixing with phosphate buffer (300 µl, 1M, pH 7.3) with addition of HCl (14 µl, 12M). The sample was transferred to an NMR spectrometer and the acquisition was started 30 s after the dissolution recording a time series of 1D spectra to follow signal decay. From the NMR spectra it was clear that the hydrolysis was complete at the start of the acquisition. The pH was 6.8 after neutralization and the recorded $T_1$ of the hydrolysis product was 45 s.

The invention claimed is:

1. A composition comprising:
   acetic anhydride,
   a DNP agent, and
   a gadolinium complex of formula (A):

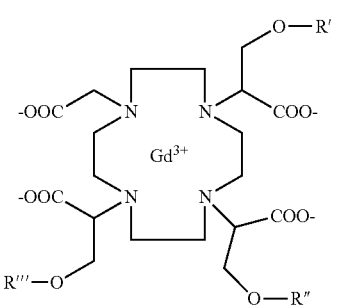

(A)

wherein:
R', R" and R'" are independently selected from: optionally substituted phenyl, $(C_1-C_6)$alkylene-phenyl and $C_6-C_{10}$ heterocyclic ring.

2. A composition according to claim 1 wherein the gadolinium complex is [[α1,α4,α7-tris [(phenylmethoxy) methyl]-1,4,7,10-tetraazacyclododecane-1,4,7,10-tetraacetato(4-)]gadolinate(1-)]hydrogen, of formula (I):

Formula (I)

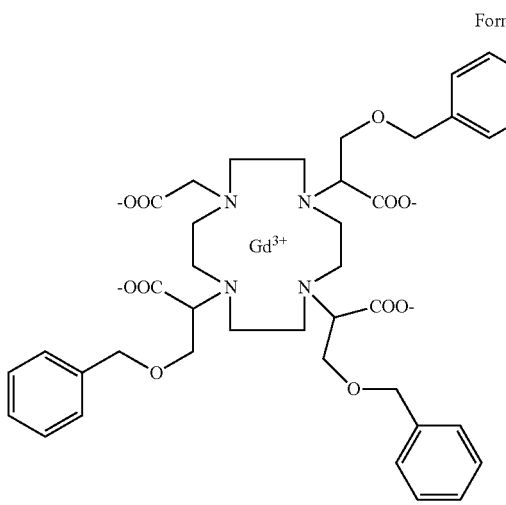

3. A composition according to claim 1 wherein the DNP agent is a compound of formula (B):

Formula (B)

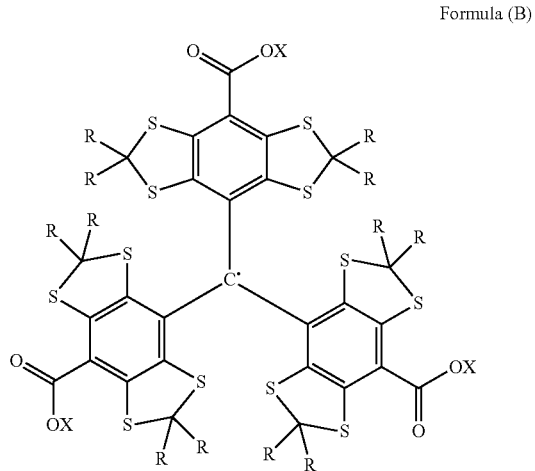

wherein:
R the same or different, represents a straight chain or branched C1-C6-alkyl group optionally deuterated and substituted by one or more hydroxyl group, methoxy group, or a group of formula —$(CH_2)_n$—O—R2, wherein n is 1, 2 or 3;

R2 is a straight or branched C1-C6-alkyl group, optionally substituted by one or more hydroxyl groups or methoxy groups; and X is independently selected from: H, an alkaline metal, an optionally substituted straight or branched C1-C6 alkyl group, optionally interrupted by Sulphur or Oxygen atoms, and an optionally substituted aliphatic or aromatic C3-C8 cyclic group or hetero group.

4. A composition according to claim 2 wherein the DNP agent is a compound of formula (B):

Formula (B)

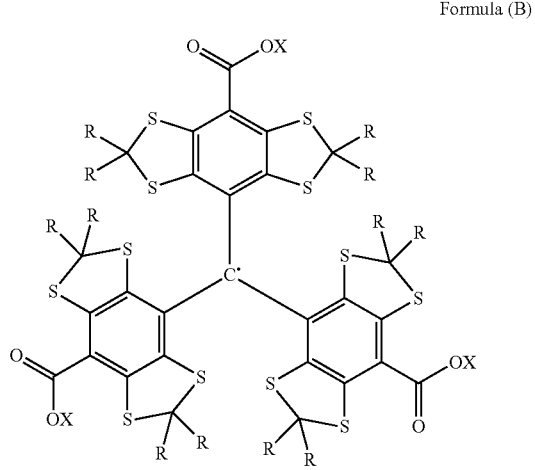

wherein:
R the same or different, represents a straight chain or branched C1-C6-alkyl group optionally deuterated and substituted by one or more hydroxyl group, methoxy group, or a group of formula —$(CH_2)_n$—O—R2, wherein n is 1, 2 or 3;

R2 is a straight or branched C1-C6-alkyl group, optionally substituted by one or more hydroxyl groups or methoxy groups; and X is independently selected from: H, an alkaline metal, an optionally substituted straight or branched C1-C6 alkyl group, optionally interrupted by Sulphur or Oxygen atoms, and an optionally substituted aliphatic or aromatic C3-C8 cyclic group or hetero group.

5. A composition according to claim 3 wherein in formula (B) R is CH3or CD3.

6. A composition according to claim 4 wherein in formula (B) R is CH3or CD3.

7. A process for the preparation of liquid hyperpolarised acetic acid, said process comprising; the steps of:
   a) subjecting the composition as defined in claim 1 to dynamic nuclear polarisation (DNP) to obtain hyperpolarised acetic anhydride; and
   b) contacting the hyperpolarised acetic anhydride of step a) with an aqueous carrier to transform said hyperpolarised acetic anhydride into hyperpolarised acetic acid; and optionally
   c) removing the gadolinium complex of formula (A) and the DNP agent.

8. A process for the preparation of liquid hyperpolarised acetic acid, said process comprising, the steps of:
   a) subjecting the composition as defined in claim 2 to dynamic nuclear polarisation (DNP) to obtain hyperpolarised acetic anhydride; and
   b) contacting the hyperpolarised acetic anhydride of step a) with an aqueous carrier to transform said hyperpolarised acetic anhydride into hyperpolarised acetic acid; and optionally
   c) removing the gadolinium complex of formula (A) and the DNP agent.

9. A process for the preparation of liquid hyperpolarised acetic acid, said process comprising the steps of:
   a) subjecting the composition as defined in claim 3 to dynamic nuclear polarisation (DNP) to obtain hyperpolarised acetic anhydride; and
   b) contacting the hyperpolarised acetic anhydride of step a) with an aqueous carrier to transform said hyperpolarised acetic anhydride into hvperpolarised acetic acid; and optionally
   c) removing the gadolinium complex of formula (A) and the DNP agent.

10. A process for the preparation of liquid hyperpolarised acetic acid, said process comprising the steps of:
    a) subjecting the composition as defined in claim 4 to dynamic nuclear polarisation (DNP) to obtain hyperpolarised acetic anhydride; and
    b) contacting the hyperpolarised acetic anhydride of step a) with an aqueous carrier to transform said hyperpolarised acetic anhydride into hyperpolarised acetic acid; and optionally
    c) removing the gadolinium complex of formula (A) and the DNP agent.

11. A process for the preparation of liquid hyperpolarised acetic acid, said process comprising the steps of:
    a) subjecting the composition as defined in claim 5 to dynamic nuclear polarisation (DNP) to obtain hyperpolarised acetic anhydride; and
    b) contacting the hyperpolarised acetic anhydride of step a) with an aqueous carrier to transform said hyperpolarised acetic anhydride into hyperpolarised acetic acid; and optionally
    c) removing the gadolinium complex of formula (A) and the DNP agent.

12. A process for the preparation of liquid hyperpolarised acetic acid, said process comprising the steps of:
    a) subjecting the composition as defined in claim 6 to dynamic nuclear polarisation (DNP) to obtain hyperpolarised acetic anhydride; and
    b) contacting the hyperpolarised acetic anhydride of step a) with an aqueous carrier to transform said hyperpolarised acetic anhydride into hyperpolarised acetic acid; and optionally
    c) removing the gadolinium complex of formula (A) and the DNP agent.

13. The method of claim 7 further comprising the steps of:
    a) administering the hyperpolarised acetic acid to a subject;
    b) submitting the subject, which has been positioned in a MRI system, to a radiation frequency selected to excite nuclear spin transitions in a non-zero nuclear spin nuclei of said hyperpolarised acetic acid; and
    c) recording a MR signal from said excited nuclei.

14. The method of claim 8 further comprising the steps of:
    a) administering the hyperpolarised acetic acid to a subject;
    b) submitting the subject, which has been positioned in a MRI system, to a radiation frequency selected to excite nuclear spin transitions in a non-zero nuclear spin nuclei of said hyperpolarised acetic acid; and
    c) recording a MR signal from said excited nuclei.

15. The method of claim 9 further comprising the steps of:
    a) administering the hyperpolarised acetic acid to a subject;
    b) submitting the subject, which has been positioned in a MRI system, to a radiation frequency selected to excite nuclear spin transitions in a non-zero nuclear spin nuclei of said hyperpolarised acetic acid; and
    c) recording a MR signal form a said excited nuclei.

16. The method of claim 10 further comprising the steps of:
    a) administering the hyperpolarised acetic acid to a subject;
    b) submitting the subject, which has been positioned in a MRI system, to a radiation frequency selected to excite nuclear spin transitions in a non-zero nuclear spin nuclei of said hyperpolarised acetic acid; and
    c) recording a MR signal from said excited nuclei.

17. The method of claim 11 further comprising the steps of:
    a) administering the hyerpolarised acetic acid to a subject;
    b) submitting the subject, which has been positioned in a MRI system, to a radiation frequency selected to excite nuclear spin transitions in a non-zero nuclear spin nuclei of said hyperpolarised acetic acid; and
    c) recording a MR signal from said excited nuclei.

18. The method of claim 12 further comprising the steps of:
    a) administering the hyperpolarised acetic acid to a subject;
    b) submitting the subject, which has been positioned in a MRI system, to a radiation frequency selected to excite nuclear spin transitions in a non-zero nuclear spin nuclei of said hyperpolarised acetic acid; and
    c) recording a MR signal from said excited nuclei.

* * * * *